United States Patent

Crismore et al.

[19]

[11] Patent Number: 5,997,817
[45] Date of Patent: Dec. 7, 1999

[54] ELECTROCHEMICAL BIOSENSOR TEST STRIP

[75] Inventors: William F. Crismore; Nigel A. Surridge, both of Indianapolis; Daniel R. McMinn, Fishers; Richard J. Bodensteiner, Indianapolis; Eric R. Diebold, Fishers; R. Dale Delk, Muncie; David W. Burke, Carmel; Jiaxiong Jason Ho, Carmel; Robert Kitchel Earl, Carmel; Brian A. Heald, Fishers, all of Ind.

[73] Assignee: Roche Diagnostics Corporation, Indianapolis, Ind.

[21] Appl. No.: 08/985,840

[22] Filed: Dec. 5, 1997

[51] Int. Cl.⁶ .................................................. G01N 33/48
[52] U.S. Cl. ..................... 422/58; 422/82.01; 204/403; 324/692; 435/817
[58] Field of Search ........................... 422/58, 61, 82.01, 422/82.02, 76; 436/63, 149, 150, 151; 204/403, 416; 324/444, 692; 435/817

[56] References Cited

U.S. PATENT DOCUMENTS

| 4,224,125 | 9/1980 | Nakamura et al. . |
| 4,254,083 | 3/1981 | Columbus . |

(List continued on next page.)

FOREIGN PATENT DOCUMENTS

| 0 010 456 B1 | 4/1980 | European Pat. Off. . |
| 0 080 304 A1 | 6/1983 | European Pat. Off. . |
| 0 127 958 B1 | 12/1984 | European Pat. Off. . |
| 0 136 362 B1 | 4/1985 | European Pat. Off. . |
| 0 170 375 A2 | 2/1986 | European Pat. Off. . |
| 0 206 218 A2 | 12/1986 | European Pat. Off. . |
| 0 230 472 A1 | 8/1987 | European Pat. Off. . |
| 0 359 831 A1 | 3/1990 | European Pat. Off. . |
| 0 400 918 A1 | 12/1990 | European Pat. Off. . |
| 0 537 761 A2 | 4/1993 | European Pat. Off. . |
| 0 732 406 A1 | 9/1996 | European Pat. Off. . |
| 60-173457 | 9/1985 | Japan . |
| 60-173458 | 9/1985 | Japan . |
| 60-173459 | 9/1985 | Japan . |

(List continued on next page.)

OTHER PUBLICATIONS

Williams et al., "Electrochemical–Enzymatic Analysis of Blood Glucose and Lactate," Analytical Chemistry, Monsanto Company (Everett, Massachusetts), vol. 42 (No. 1), pp. 118–121 (Jan. 1970).

Jonathan Lee Talbott, "Enzymatic Amperometry of Glucose," a Ph.D. Dissertation for The Pennsylvania State University, The Graduate School, Department of Chemistry (Jan. 1988).

Nankai et al., "disposable Glucose Sensor Using Hexacyanoferrate(III) As A Mediator," Japanese Sensor Newsletter, Edison Sensor Technology Center, Case Western Reverse University (Cleveland, Ohio), vol. 3 (No. 1), pp. 16–20 (Mar. 1989).

*Primary Examiner*—Lyle A. Alexander
*Attorney, Agent, or Firm*—Richard T. Knauer; Roche Diagnostics Corporation

[57] ABSTRACT

An electrochemical biosensor test strip with four new features. The test strip includes an indentation for tactile feel as to the location of the strips sample application port. The sample application port leads to a capillary test chamber, which includes a test reagent. The wet reagent includes from about 0.2% by weight to about 2% by weight polyethylene oxide from about 100 kilodaltons to about 900 kilodaltons mean molecular weight, which makes the dried reagent more hydrophilic and sturdier to strip processing steps, such as mechanical punching, and to mechanical manipulation by the test strip user. The roof of the capillary test chamber includes a transparent or translucent window which operates as a "fill to here" line, thereby identifying when enough test sample (a liquid sample, such as blood) has been added to the test chamber to accurately perform a test. The test strip may further include a notch located at the sample application port. The notch reduces a phenomenon called "dose hesitation".

32 Claims, 5 Drawing Sheets

U.S. PATENT DOCUMENTS

| | | | |
|---|---|---|---|
| 4,413,407 | 11/1983 | Columbus | 29/825 |
| 4,473,457 | 9/1984 | Columbus . | |
| 4,543,326 | 9/1985 | Miyashita et al. . | |
| 4,684,445 | 8/1987 | Seshimoto et al. | 422/99 |
| 4,758,323 | 7/1988 | Davis et al. . | |
| 4,810,633 | 3/1989 | Bauer et al. . | |
| 4,820,399 | 4/1989 | Senda et al. . | |
| 4,830,959 | 5/1989 | McNeil et al. . | |
| 4,894,137 | 1/1990 | Takizawa et al. . | |
| 4,897,173 | 1/1990 | Nankai et al. . | |
| 4,959,305 | 9/1990 | Woodrum . | |
| 4,999,582 | 3/1991 | Parks et al. . | |
| 4,999,632 | 3/1991 | Parks . | |
| 5,120,420 | 6/1992 | Nankai et al. . | |
| 5,141,868 | 8/1992 | Shanks et al. . | |
| 5,192,415 | 3/1993 | Yoshioka et al. . | |
| 5,243,516 | 9/1993 | White . | |
| 5,264,103 | 11/1993 | Yoshioka . | |
| 5,288,636 | 2/1994 | Pollmann et al. | 435/288 |
| 5,352,351 | 10/1994 | White et al. . | |
| 5,354,447 | 10/1994 | Uenoyama et al. . | |
| 5,366,609 | 11/1994 | White et al. . | |
| 5,395,504 | 3/1995 | Saurer et al. . | |
| 5,405,511 | 4/1995 | White et al. . | |
| 5,413,690 | 5/1995 | Kost et al. | 204/403 |
| 5,437,999 | 8/1995 | Diebold et al. | 435/288 |
| 5,438,271 | 8/1995 | White et al. . | |
| 5,508,171 | 4/1996 | Walling et al. . | |
| 5,575,895 | 11/1996 | Ikeda et al. . | |
| 5,798,031 | 8/1998 | Charlton et al. . | |

FOREIGN PATENT DOCUMENTS

| | | |
|---|---|---|
| 61-90050 | 5/1986 | Japan . |
| 63-58149 | 3/1988 | Japan . |
| 63-128252 | 5/1988 | Japan . |
| 63-139246 | 6/1988 | Japan . |
| 63-317757 | 12/1988 | Japan . |
| 63-317758 | 12/1988 | Japan . |
| 64-23153 | 1/1989 | Japan . |
| 1-114746 | 5/1989 | Japan . |
| 1-114747 | 5/1989 | Japan . |
| 1-134244 | 5/1989 | Japan . |
| 1-156658 | 6/1989 | Japan . |
| 2 154 003 | 8/1985 | United Kingdom . |
| 2 204 408 | 11/1988 | United Kingdom . |
| WO89/08713 | 9/1989 | WIPO . |

ELECTROCHEMICAL BIOSENSOR TEST STRIP

FIELD OF THE INVENTION

This invention relates to a biosensor and its use in the detection or measurement of analytes in fluids.

BACKGROUND OF THE INVENTION

The prior art includes test strips, including electrochemical biosensor test strips, for measuring the amount of an analyte in a fluid.

Particular use of such test strips has been made for measuring glucose in human blood. Such test strips have been used by diabetics and health care professionals for monitoring their blood glucose levels. The test strips are usually used in conjunction with a meter, which measures light reflectance, if the strip is designed for photometric detection of a dye, or which measures some electrical property, such as electrical current, if the strip is designed for detection of an electroactive compound.

However, test strips that have been previously made present certain problems for individuals who use them. For example, test strips are relatively small and a vision impaired diabetic may have great difficulty properly adding a sample of blood to the sample application area of the test strip. It would be useful for the test strip to be made so that vision impaired persons could easily dose the test strip.

When the test strip is a capillary fill device, that is, when the chemical reaction chamber of the test strip is a capillary space, particular problems can occur with filling the chamber smoothly and sufficiently with the liquid sample to be tested. Due to the smallness of the capillary space and the composition of materials used to make the test strip, the test sample may hesitate entering the capillary reaction chamber. Further, insufficient sample may also be drawn into the capillary reaction chamber, thereby resulting in an inaccurate test result. It would be very useful if such problems could be minimized.

Finally, test strips, especially those used by diabetics for measuring blood glucose are mass produced. Processes, such as mechanical punching, used to make these test strips can cause a test reagent that has been dried onto a surface of the testing area to crack or break, thereby causing reagent loss or improper placement of the reagent within the strip. It would also be useful to design a test reagent that could withstand processing steps, such as mechanical punching.

The electrochemical, biosensor test strip of the present invention provides solutions to these above-stated problems found in prior art test strips.

SUMMARY OF THE INVENTION

The invention is an improved electrochemical biosensor test strip with four new, highly advantageous features.

The first new feature is an indentation along one edge of the test strip for easy identification of the sample application port for vision impaired persons or for use in zero or low lighting conditions.

The test strip has a capillary test chamber, and the roof of the test chamber includes the second new feature of the biosensor test strip. The second new feature is a transparent or translucent window which operates as a "fill to here" line, thereby identifying when enough test sample (a liquid sample, such as blood) has been added to the test chamber to accurately perform a test. The window defines the minimum sample amount, or dose, required to accurately perform a test, and, therefore, represents a visual failsafe which reduces the chances of erroneous test results due to underdosing of a test strip.

The length and width of the window are shorter than the length and width of the capillary test chamber. The window is dimensioned and positioned so that it overlays the entire width of the working electrode and at least about 10% of the width of the counter or reference electrode of the biosensor test strip. Preferably, the area of the roof surrounding the window is colored in a way that provides good color contrast between the sample, as observed through the window, and the roof area surrounding the window for ease of identifying sufficient dosing of the strip.

The third new feature of the test strip is the inclusion of a notch, or multiple notches, located at the sample application port. A notch is created in both the first insulating substrate and the roof of the strip. These notches are dimensioned and positioned so that they overlay one another in the test strip. These notches reduce a phenomenon called "dose hesitation". When a sample is added to the sample application port of a notchless strip, the sample can hesitate in its introduction into the capillary test chamber. This "dose hesitation" adds to the testing time. When the test strip includes a notch, dose hesitation is reduced. Further, including the notch in both the first insulating substrate and the roof makes it possible for the test sample to approach the sample application port from a wide variety of angles. The angle of approach for the test sample would be more limited if the notch were only in the roof.

Finally, the fourth new feature of the test strip is a reagent that includes polyethylene oxide from about 100 kilodaltons to about 900 kilodaltons mean molecular weight at concentrations from about 0.2% (weight:weight) to about 2% (weight:weight), which makes the dried reagent more hydrophilic and sturdier. With the inclusion of polyethylene oxide, the test reagent can more readily withstand mechanical punching during strip assembly and mechanical manipulation by the user of the test strip. Further, the dried reagent, which will include from about 1.75% (weight:weight) to about 17.5% (weight:weight) polyethylene oxide, can easily redissolve, or resuspend, when an aqueous test sample is added to the strip's test chamber.

DESCRIPTION OF THE INVENTION

Figure 1:
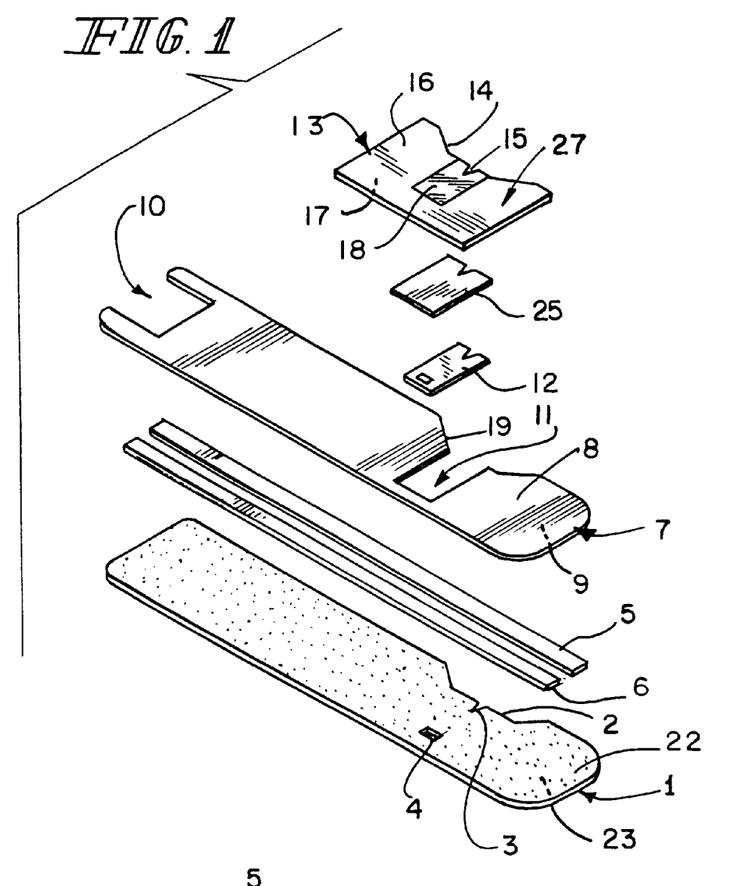
FIG. 1 is an exploded view of a preferred embodiment of the present invention.
Figure 2:
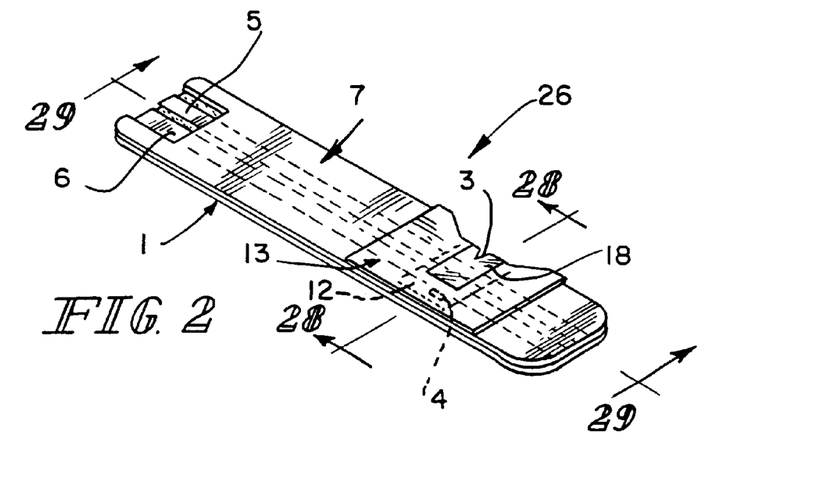
FIG. 2 shows a fully assembled, preferred test strip.

The components of a preferred embodiment of the present inventive biosensor are shown in FIGS. 1, 2, 4 and 5. The biosensor includes first insulating substrate 1, which has first surface 22 and second surface 23. Insulating substrate 1 may be made of any useful insulating material. Typically, plastics, such as vinyl polymers, polyimides, polyesters, and styrenics provide the electrical and structural properties which are desired. First insulating substrate 1 further includes indentation 2, notch 3, and vent hole 4. Because the biosensor shown in FIG. 1 is intended to be mass produced from rolls of material, necessitating the selection of a material which is sufficiently flexible for roll processing and at the same time sufficiently stiff to give a useful stiffness to the finished biosensor, a particularly preferred first insulating substrate 1 is 7 mil thick MELINEX 329 plastic, a polyester available from ICI Films (3411 Silverside Road, PO Box 15391, Wilmington, Del. 19850).

As shown in FIG. 1, electrically conductive tracks 5 and 6 are laid down onto first surface 22 of first insulating substrate 1. Track 5 may be a working electrode, made of electrically conducting materials such as palladium, platinum, gold, carbon, and titanium. Track 6 may be a counter electrode, made of electrically conducting materials such as palladium, platinum, gold, silver, silver containing alloys, nickel-chrome alloys, carbon, titanium, and copper. Noble metals are preferred because they provide a more constant, reproducible electrode surface. Palladium is particularly preferred because it is one of the more difficult noble metals to oxidize and because it is a relatively inexpensive noble metal.

Preferably, electrically conductive tracks 5 and 6 are deposited on an insulative backing, such as polyimide or polyester, to reduce the possibility of tearing the electrode material during handling and manufacturing of the test strip. An example of such conductive tracks is a palladium coating with a surface resistance of less than 5 ohms per square on UPILEX polyimide backing, available from Courtalds-Andus Performance Films in Canoga Park, Calif.

Electrically conductive tracks 5 and 6 represent the electrodes of the biosensor test strip. These electrodes must be sufficiently separated so that the electrochemical events at one electrode do not interfere with the electrochemical events at the other electrode. The preferred distance between electrodes 5 and 6 is about 1.2 millimeters (mm).

In the test strip shown in FIG. 1, electrically conductive track 5 would be the working electrode, and electrically conductive track 6 would be a counter electrode or reference electrode. Track 6 would be a reference electrode if made of typical reference electrode materials, such as silver/silver chloride. In a preferred embodiment, track 5 is a working electrode made of palladium, and track 6 is a counter electrode that is also made of palladium and is substantially the same size as the working electrode.

Three electrode arrangements are also possible, wherein the strip includes an additional electrically conductive track located between conductive track 6 and vent hole 4. In a three electrode arrangement, conductive track 5 would be a working electrode, track 6 would be a counter electrode, and the third electrode between track 6 and vent hole 4 would be a reference electrode.

Overlapping conductive tracks 5 and 6 is second insulating substrate 7. Second insulating substrate 7 is made of a similar, or preferably the same, material as first insulating substrate 1. Substrate 7 has a first surface 8 and a second surface 9. Second surface 9 is affixed to the surface of substrate 1 and conductive tracks 5 and 6 by an adhesive, such as a hot melt glue. An example of such glue is DYNAPOL S-1358 glue, available from Hüls America, Inc., 220 Davidson Street, PO Box 6821, Somerset, N.J. 08873. Substrate 7 also includes first opening 10 and second opening 11. First opening 10 exposes portions of conductive tracks 5 and 6 for electrical connection with a meter, which measures some electrical property of a test sample after the test sample is mixed with the reagent of the test strip. Second opening 11 exposes a different portion of conductive tracks 5 and 6 for application of test reagent 12 to those exposed surfaces of tracks 5 and 6. (In FIG. 1, the entire width of conductive tracks 5 and 6 are exposed by opening 11. However, it is also possible to expose only a portion of the width of conductive track 6, which is either a counter electrode or a reference electrode, as long as at least about 10% of the width is exposed by opening 11.) Additionally, second insulating substrate 7 includes indentation 19, which coincides with indentation 2 as shown in FIG. 1.

Test reagent 12 is a reagent that is specific for the test to be performed by the test strip. Reagent 12 may be applied to the entire exposed surface area of conductive tracks 5 and 6 in the area defined by second opening 11. Other applications of reagent 12 in this region are also possible. For example, if conductive track 6 in this region of the strip has a reference electrode construction, such as silver/silver chloride, then test reagent 12 may only need to cover the exposed area of working electrode 5 in this region. Further, the entire exposed area of an electrode may not need to be covered with test reagent as long as a well defined and reproducible area of the electrode is covered with reagent.

Overlaying a portion of first surface 8 and second opening 11 is roof 13. Roof 13 includes indentation 14 and notch 15. Indentation 14 and notch 15 are shaped and positioned so that they directly overlay indentations 2 and 19, and notch 3. Roof 13 may be made of a plastic material, such as a transparent or translucent polyester foil from about 2 mil to about 6 mil thickness. Roof 13 has first surface 16 and second surface 17. Second surface 17 of roof 13 is affixed to first surface 8 of second insulating substrate 7 by a suitable adhesive, such as 3 M 9458 acrylic, available from 3M, Identification and Converter Systems Division, 3M Center, Building 220-7W-03, St. Paul, Minn. 55144.

Preferably, roof 13 further includes transparent or translucent window 18. Window 18 is dimensioned and positioned so that when roof 13 is affixed to second insulating substrate 7, the window overlays the entire width of conductive track 5 and at least about ten percent of the width of conductive track 6.

Second surface 17 of roof 13, the edges of opening 11, and first surface 22 of insulating substrate 1 (and conductive tracks 5 and 6 affixed to first surface 22 of substrate 1) define a capillary testing chamber. The length and width of this capillary chamber are defined by the length and width of opening 11 and the height of the chamber is defined by the thickness of second insulting substrate 7.

A preferred test strip may be manufactured as shown by the process illustrated by FIGS. 3*a*–3*i*. A sheet of insulative substrate material 21 (MELINEX 329, 7 mil thickness, available from ICI) is coated on one side with hotmelt adhesive (DYNAPOL S-1358, available from Hüls). (FIG. 3*a*) Sheet 21 is cut along line 24, thereby forming first insulating substrate 1, coated with adhesive on first surface 22, and second insulating substrate 7, coated with adhesive on second surface 2. (FIGS. 3*b* and 3 *c*) First opening 10 and second opening 11 are created in substrate 7 by die punching. (FIG. 3*d*) Next, electrically conductive tracks 5 and 6, made of palladium on Upilex backing (available from Courtalds-Andus Performance Films), are unspooled from reels precut to about 1.5 millimeters width and laid down on surface 22 of substrate 1 so that the Upilex backing is adjacent to surface 22. Surface 9 of substrate 7 is laid adjacent to surface 22 of substrate 1 and to conductive tracks 5 and 6, thereby forming the sandwich structure shown in FIG. 3*e*. This sandwich structure is heat sealed.

A test reagent 12 is then dispensed into opening 11 and dried. (FIG. 3f) After reagent 12 is dried, vent hole 4 is created by a die punch. (FIG. 3g) Next, roof 13, which includes hydrophilic coating 25 and window 18, is laid down over opening 11 in a manner such that window 18 overlaps the entire width of conductive track 5 and about one half of the width of conductive track 6. Roof 13 is released from a release liner and adhesively affixed to surface 8 as shown in FIG. 3h.

Figure 3A:
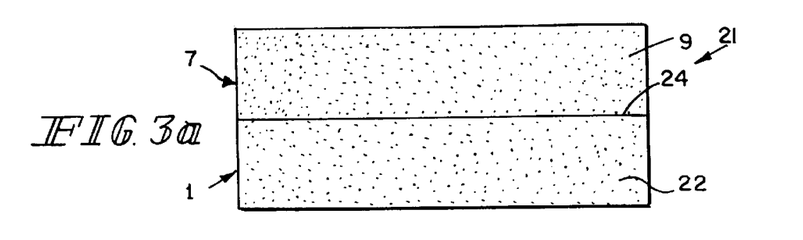
FIGS. 3a–3i represent a preferred method of making the inventive test strip.
Figure 3B:
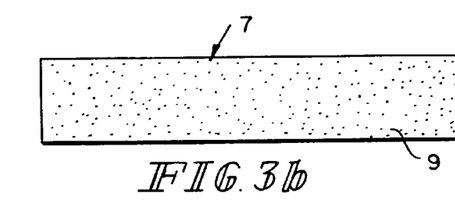
Figure 3C:
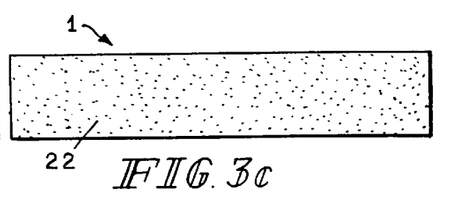
Figure 3D:
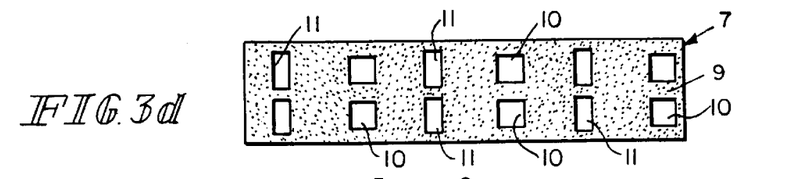
Figure 3E:
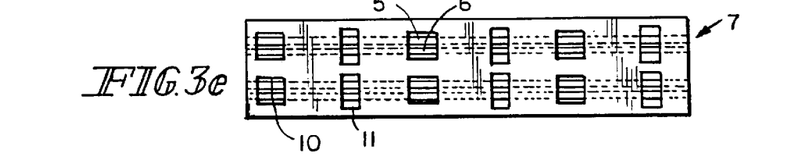
Figure 3F:
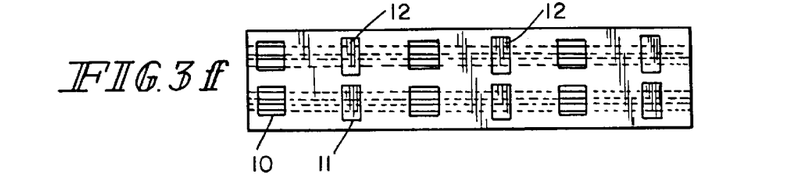
Figure 3G:
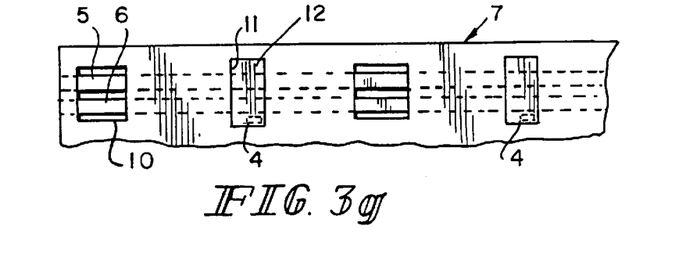
Figure 3H:
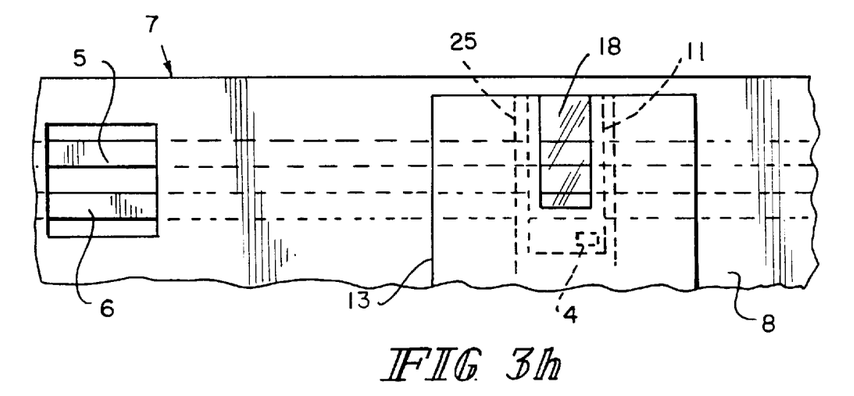
Figure 3I:
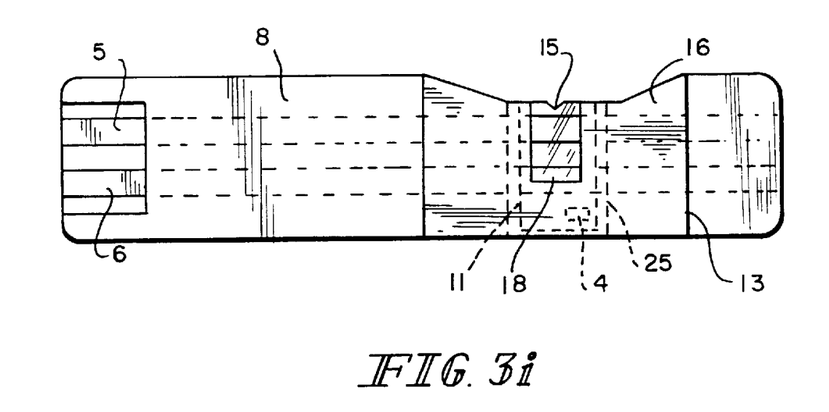
Figure 4:
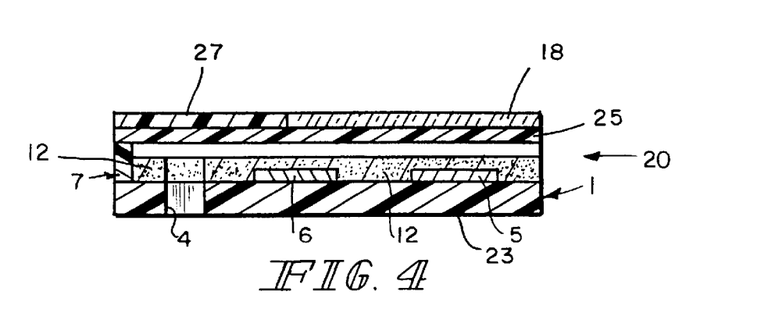
FIG. 4 is a cross sectional view of the test strip of FIG. 2 through line 28—28.
Figure 5:
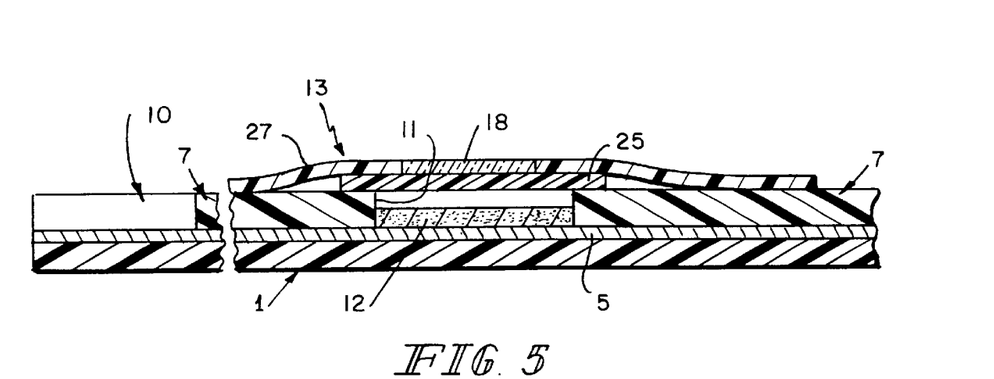
FIG. 5 is a cross sectional view of the test strip of FIG. 2 through line 29—29.

Finally, individual test strips are punched out by a die punch as shown in FIG. 3i. The die punch may punch out test strips with or without notch 15. If notch 15 is included, the preferred angle of the vertex is 105°. Other angles, such as from about 45° to about 105°, are also possible for notch 15. Further, notch 15 may be a single notch or multiple notches.

As noted above, test reagent 12 is dispensed into the area of the test strip defined by cutout 11. In the manufacturing process described above, it is preferred to provide corona treatment of opening 11 before test reagent 12 is applied. The application of corona treatment serves to increase the surface energy of the portion of surface 22 and conductive tracks 5 and 6 exposed by opening 11, encouraging uniform spreading of reagent 12, and to pre-clean the portion of conductive tracks 5 and 6 exposed by opening 11. Pre-cleaning of conductive tracks 5 and 6 has been found to significantly improve the performance of the test strip. Corona treatment may be applied at Watt densities ranging from about 20 to about 90 watts per centimeter per second (W/cm/s) with an arc gap of about 1 millimeter (0.040 inch).

In the preferred method, the corona treatment is applied in blanket form over the surfaces shown in FIG. 3e at the above described watt densities. The treatment is most effective if applied within 5 minutes of reagent 12 application and is typically practiced within 45 seconds of reagent 12 application.

It is advantageous to reduce the effects of corona treatment on surface 8 in order to ensure that reagent 12 will fully coalesce in opening 11 and does not have a greater affinity for surface 8 than for the portion of surface 22 and conductive tracks 5 and 6 exposed by opening 11. A corona dissipation process, which allows for the selective reduction of the effects of a blanket corona treatment process, is incorporated to reduce the effects of the treatment on areas of the web (the sheet of test strips being processed) outside of opening 11. This corona dissipation process consists of applying, a thin film of deionized water such that the water contacts surface 8, but will not contact openings 10 and 11. Application of the thin film of water, which is preferably from about 1.5 microns to about 3.0 microns thickness (about 9.1 grams of water per square meter), may be accomplished via wick pad, flexographic print, or other commercially available coating application methods. The thin film of water is then dried from the surface, using forced convection or infrared methods just prior to application of reagent 12. The net effect of this treatment is that the surface energy of surface 8 is effectively reduced to less than 62 dyne prior to the application of reagent 12 while the surface of area within opening 11 is maintained at it's post corona treatment surface energy.

In the preferred embodiment, test reagent 12 is formulated for the measurement of glucose in a human blood sample. A protocol for the preparation of a liter of a preferred glucose reagent utilizing the enzyme quinoprotein (pyrroloquinoline quinone (PQQ)-containing) glucose dehydrogenase and the redox mediator ferricyanide is shown immediately below. (Quinoprotein glucose dehydrogenase is Enzyme Commission No. 1.1.99.17.)

Step 1: Prepare a solution of NATROSOL in deionized water. This is accomplished by adding 0.45 grams (g) of NATROSOL-250M (a microcrystalline hydroxyethylcellulose available from Aqualon) to 414 g of deionzied water while stirring at a speed of no less than 250 revolutions per minute (rpm) for a period of no less than 30 minutes. Mixing is best accomplished with an overhead rotating impeller using a three or four bladed turbine type propeller. The selection of propeller size and configuration is largely based on the radius of the mixing vessel being used. The selected propeller will typically have a radius greater than 75% of the radius of the mixing vessel.

Step 2: To the solution from Step 1, 5.6 g of AVICEL RC-591F (a microcrystalline cellulose available from FMC Corp.) is dispersed by gradually adding this AVICEL to the solution while mixing at a speed of no less than 570 rpm for no less than 60 minutes.

Step 3: To the mixture from Step 2, 8.4 g polyethylene oxide (300 kilodalton mean molecular weight) is added gradually while mixing at a speed of no less than 690 rpm for a period of no less than 45 minutes.

Step 4: A buffer solution is prepared by adding 12.1 g of monobasic potassium phosphate (anhydrous) and 21.3 g of dibasic potassium phosphate (anhydrous) to 450 g of deionized water.

Step 5: A 50 g aliquot of the buffer solution is removed from the preparation of Step 4. To this 50 g aliquot, 12.5 mg of coenzyme PQQ (available from Fluka) is added. This solution is stirred until the coenzyme is completely dissolved. (A magnetic stir bar and magnetic stir plate are preferred for enzyme preparation.)

Step 6: To the solution from Step 5, 1.21 million units of the apoenzyme of quinoprotein glucose dehydrogenase is added gradually while stirring at a low speed (less than 400 rpm on a magnetic stir plate) to prevent foaming. The resulting solution is mixed for no less than 2 hours to allow the association of the enzyme and coenzyme to stabilize, thereby resulting in a solution of quinoprotein glucose dehydrogenase.

Step 7: To the buffer solution from Step 4, 59.1 g of potassium ferricyanicle is added. Next, 6.2 g of sodium succinate is added. The resulting solution is mixed until all solutes are completely dissolved. After dissolution, the pH of the solution is assessed and is required to be approximately 6.76 plus or minus 0.05.

Step 8: The solution from Step 7 is gradually incorporated into the mixture from Step 3, while mixing at a rate of no less than 190 rpm.

Step 9: To the mixture from Step 8, 20 g trehalose is added, while mixing at a rate of no more than 190 rpm for a period of not less than 10 minutes.

Step 10 : 0.35 g of TRITON X-100 surfactant, available from Boehringer Mannheim Biochemicals, is added to the mixture from Step 9, while mixing at a rate of no more than 190 rpm. This mixture must continue mixing for no less than 5 minutes.

Step 11: The enzyme solution from Step 6 is added to the mixture from Step 10 and the now complete reagent is mixed at a rate of no less than 190 rpm for a period of no less than 30 minutes.

Step 12: The reagent can now be filtered, as needed by the manufacturing equipment, by passing it through a 100 micron sieve bag or through a 100 micron filter integral to a pumping system.

The apoenzyme of quinoprotein glucose dehygrogenase, specified above, is obtained from Boehringer Mannheim GmbH in Germany (Boehringer Marinheim GmbH identification number 1464221). Alternatively, this apoenzyme may be obtained from Acinetobacter Calcoaceticus by the following protocol, recited in Duine et al., *FEBS Letters*, vol. 108, no. 2, pps. 443–46.

Acinetobacter Calcoaceticus are grown on a mineral salt medium supplemented with 0.02 molar (M) sodium succinate or 0.10 M ethanol at 22° C. with good aeration. The cells are harvested at the end of the logarithmic phase and a wet-cell yield of ~4 g/l can be obtained.

Frozen cells (10 g) are thawed and mixed with 15 milliliters (ml) of 36 millimolar (mM) Tris/39 mM glycine buffer. After adding 6 milligrams (mg) lysozyme, the suspension is stirred at room temperature for 15 min. and centrifuged for 10 min. at 48,000×g. The supernatant is discarded and the pellet extracted twice with 36 mM Tris/39 mM glycine buffer, containing 1% TRITON X-100 surfactant. The supernatants of the centrifugation steps are combined and used immediately.

The cell-free extract is added to a DEAE-Sephacel column (13×2.2 centimeters (cm)), equilibrated with 36 mM Tris/39 mM glycine buffer, containing 1% TRITON X-100 surfactant and the column is washed with the same buffer. The enzyme does not adhere to the column material and the combined active fractions are titrated with 2 M acetic acid to pH 6.0. This solution is added immediately to a column of CM-Sepharose CL-6 B (5×1 cm), equilibrated with 5 mM potassium phosphate (pH 6.0). After washing the column with the same buffer until no TRITON X-100 surfactant is present in the eluate, the enzyme is eluted with 0.1 M potassium phosphate (pH 7.0).

The enzyme is then dialyzed against 0.1 M sodium acetate (pH 4.5), containing 3 M potassium bromide at 4° C. for 72 hours. The enzyme is then dialyzed against 0.02 M potassium phosphate (pH 7.0) for 12 hours, resulting in the apoenzyme.

In the preferred test strip, opening 11 is about 3.2 millimeters by about 6.7 millimeters. In the preferred embodiment of a glucose test strip, 4.5 microliters of test reagent made by the above protocol is added to opening 11. (See FIG. 3*f*) This amount of reagent will substantially cover the exposed surfaces of conductive tracks 5 and 6 in opening 11. Test reagent 12 is then dried at about 70° C. for about 1 to 2 minutes.

The resulting, preferred, dried glucose reagent film will contain from about 2,000 to about 9,000 units of enzyme activity per gram of reagent. The preferred reagent will contain the following additional components per gram of reagent:

62.2 milligrams (mg) polyethylene oxide
 3.3 mg NATROSOL 250 M
 41.5 mg AVICEL RC-591 F
 89.4 mg monobasic potassium phosphate
 157.9 mg dibasic potassium phosphate
 437.3 mg potassium ferricyanide
 46.0 mg sodium succinate
 148.0 mg trehalose
 2.6 mg TRITON X-100 surfactant.

Importantly, including from about 0.2% by weight to about 2% by weight polyethylene oxide having a mean molecular weight from about 100 kilodaltons to about 900 kilodaltons, and preferably about 0.71% by weight polyethylene oxide having a mean molecular weight of 300 kilodaltons, in the wet reagent referred to above provides a test reagent that, when dried, is sturdier to strip processing steps, such as mechanical punching, sturdier to mechanical manipulation by test strip user, and that will redissolve or resuspend when an aqueous sample, such as human blood, is added to it. After drying, the percentage of polyethylene oxide ranges from about 1.75% (weight:weight) to about 17.5% (weight:weight). In the preferred, dried reagent, the percentage of polyethylene oxide is about 6.2% (weight:weight).

The preferred, dried, glucose reagent film thickness will be such that, in combination with the inherent properties of the test chemistry, the sensitivity of the test to interference from hematocrit variation is mitigated. In this preferred embodiment of the invention, the film thickness (as gauged by the ratio of wet reagent dispense volume to the surface area exposed by opening 11) is such that 4.5 microliters of reagent is dispensed into an area of approximately 22.5 square millimeters (the preferred area of opening 11). Including polyethylene oxide from about 100 kilodaltons to about 900 kilodaltons mean molecular weight in a film with the thickness described above, results in a sensor possessing a reduced sensitivity to hematocrit variation when glucose is measured from a human blood sample.

After test reagent 12 is dried in opening 11, roof 13 is laid over opening 11 and adhesively affixed to surface 8 as described above. Roof 13 itself is made in a separate process according to procedures described below.

Preferably, roof 13 is made of MELINEX 561 polyester foil, having a thickness of 5 mil. A substantially opaque ink is printed on first surface 16 in pattern 27 such that window 18 remains transparent or translucent. The window is positioned and dimensioned so that when the roof is affixed to surface 8, it will align with opening 11 as shown in FIG. 3*h*.

On second surface 17, an adhesive system is laminated in order that the roof may be ultimately affixed to surface 8. This adhesive system can conveniently be an acrylic adhesive such as available from many commercial sources, but preferably part number 9458 from 3M Inc.

In addition, prior to placing the roof on surface 8, a piece of coated transparent or translucent plastic, preferably a polyethylene terephthalate (PET), such as Melinex S plastic from about 0.001 to about 0.004 inch thick, is placed against the adhesive system on second surface 17, and aligned with, and extending beyond the dimensions of window 18. This coated plastic is hydrophilic coating 25. Coating 25 is specifically chosen to impart a hydrophilic nature to the internal surface of the capillary test chamber to encourage flow of an aqueous sample, such as blood, into the test chamber. Coating 25 can be chosen from many available coatings designed to present a hydrophilic surface, but product number ARCARE 8586, available from Adhesives Research, Inc., is preferred. Coating 25 also acts to prevent direct contact of the roof's adhesive to reagent 12.

Finally, roof 13 is placed onto surface 8. (See FIG. 3*h*) It is at this stage that the transparent or translucent window 18 defined by the absence of printed ink on roof 13 must align with opening 11 as shown in FIG. 3*h*. The dimensions of transparent or translucent window 18 should be chosen such that a substantial fraction of the width (greater than about 75%) of the underlying capillary channel is visible through window 18. The orthogonal dimension of window 18 should expose the entire width of the working electrode 5. Therefore, when a sample, such as blood, is introduced into the capillary test chamber, through sample application port 20, it is possible for a user of reasonable visual acuity to determine if the window is entirely full of the sample. By choosing the window dimensions as just stated it is possible to provide feedback for the user of the test strip that the strip has been sufficiently dosed with a test sample. Visual confirmation of the window being full provides assurance that a sufficient area of the working electrode is covered with sample and that a sufficient part of the counter or reference electrode 6 is also covered. This coverage of the electrodes by the test sample is important to achieving an accurate test in a capillary-fill electrochemical biosensor. This visual confirmation of sufficient dosing of the test strip provides a safeguard against erroneous test results due to undetected underdosing of the test strip.

Completed test strips 26 are used in conjunction with a meter capable of measuring some electrical property of the test sample after addition of the test sample to sample application port 20. (See FIG. 2) The electrical property being measured may be, for example, electrical current, electrical potential, electrical charge, or impedance. An example of measuring changes in electrical potential to perform an analytical test is illustrated by U.S. Pat. No. 5,413,690, the disclosure of which is hereby incorporated by reference.

An example of measuring electrical current to perform an analytical test is illustrated by U.S. Pat. Nos. 5,288,636 and 5,508,171, the disclosures of which are hereby incorporated by reference.

In the preferred embodiment, test strip 26 is connected to a meter, which includes a power source (a battery). Improvements in such meters and a biosensor system can be found in U.S. Pat. Nos. 4,999,632; 5,243,516; 5,366,609; 5,352,351; 5,405,511; and 5,438,271, the disclosures of which are hereby incorporated by reference.

Many analyte-containing fluids may be analyzed by the electrochemical test strip of the present invention. For example, analytes in human body fluids, such as whole blood, blood serum, urine and cerebrospinal fluid may be measured. Also, analytes found in fermentation products and in environmental substances, which potentially contain environmental contaminants, may be measured.

For determining the concentration of glucose in a human blood sample with the preferred test strip recited above, wherein tracks 5 and 6 are palladium of substantially the same size and the glucose reagent is the reagent specified above, a blood sample may be added to sample application port 20. The sample will be drawn into the test chamber by capillary action. Once inside the test chamber, the blood sample will mix with test reagent 12. After an incubation period of some desired time, for example, 30 seconds, a potential difference will be applied by the power source of the meter between tracks 5 and 6. In the preferred embodiment, the applied potential difference is 300 millivolts. Current may be measured at any time from 0.5 seconds to about 30 seconds after the potential difference of 300 millivolts is applied. The measured current may be correlated to the concentration of glucose in the blood sample.

Figure 6:
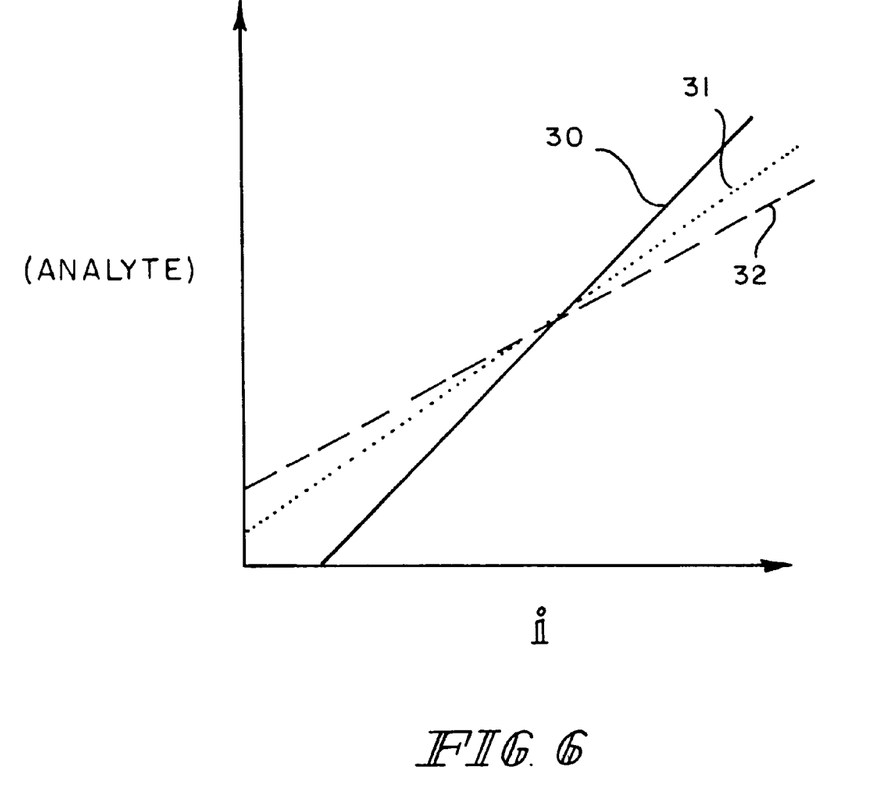
FIG. 6 illustrates hypothetical calibration curves for different lots of test strips.

The current measured during the assay of an analyte from a fluid sample may be correlated to the concentration of the analyte in the sample by application of an algorithm by the current measuring meter. The algorithm may be a simple one, as illustrated by the following example:

$$[\text{Analyte}] = C i_{7.5} + d$$

wherein [Analyte] represents the concentration of the analyte in the sample (see FIG. 6), $i_{7.5}$ is the current (in microamps) measured at 7.5 seconds after application of the potential difference applied between the electrodes, C is the slope of line 30 (FIG. 6), and d is the axis intercept (FIG. 6).

By making measurements with known concentrations of analyte, calibration curve 30 (FIG. 6) may be constructed. This calibration will be stored in the Read Only Memory (ROM) key of the meter and will be applicable to a particular lot of test strips. Lines 31 and 32 in FIG. 6 represent other hypothetical calibration curves for two other different lots of test strips. Calibration for these biosensor lots would generate slightly different values for C and d in the above algorithm.

In a preferred method for analysis of glucose from a sample of human whole blood, current measurements are made at 0.5 second intervals from 3 seconds to 9 seconds after the potential difference is applied between the electrodes. These current measurements are correlated to the concentration of glucose in the blood sample.

In this example of measuring glucose from a blood sample, current measurements are made at different times (from 3 seconds to 9 seconds after application of the potential difference), rather than at a single fixed time (as described above), and the resulting algorithm is more complex and may be represented by the following equation:

$$[\text{Glucose}] = C_1 i_1 + C_2 i_2 + C_3 i_3 + \ldots C_n i_n + d,$$

wherein $i_1$ is the current measured at the first measurement time (3 seconds after application of the 300 millivolt potential difference), $i_2$ is the current measured at the second measurement time (3.5 seconds after application of the 300 millivolt potential difference), $i_3$ is the current measured at the third measurement time (4 seconds after application of the 300 millivolt potential difference), $i_n$ is the current measured at the $n^{th}$ measurement time (in this example, at the $13^{th}$ measurement time or 9 seconds after application of the 300 millivolt potential difference), $C_1$, $C_2$, $C_3$, and $C_n$ are coefficients derived from a muiltivariate regression analysis technique, such as Principle Components Analysis or Partial Least Squares, and d is the regression intercept (in glucose concentration units).

Alternatively, the concentration of glucose in the sample being measured may be determined by integrating the curve generated by plotting current, i, versus measurement time over some time interval (for example, from 3 seconds to 9 seconds after application of the 300 millivolt potential difference), thereby obtaining the total charge transferred during the measurement period. The total charge transferred is directly proportional to the concentration of glucose in the sample being measured.

Further, the glucose concentration measurement may be corrected for differences between environmental temperature at the time of actual measurement and the environmental temperature at the time calibration was performed. For example, if the calibration curve for glucose measurement was constructed at an environmental temperature of 23° C., the glucose measurement is corrected by using the following equation:

$$[\text{Glucose}]_{corrected} = [\text{Glucose}]_{measured} \times (1 - K(T - 23° \text{ C.})),$$

wherein T is the environmental temperature (in ° C.) at the time of the sample measurement and K is a constant derived from the following regression equation:

$$Y = K(T - 23),$$

wherein $$Y = \frac{[\text{Glucose}]_{measured\ at\ 23°\ C.} - [\text{Glucose}]_{measured\ at\ T°\ C.}}{[\text{Glucose}]_{measured\ at\ T°\ C.}}$$

In order to calculate the value of K, each of a multiplicity of glucose concentrations is measured by the meter at various temperatures, T, and at 23° C. (the base case). Next, a linear regression of Y on T-23 is performed. The value of K is the slope of this regression.

Various features of the present invention may be incorporated into other electrochemical test strips, such as those disclosed in U.S. Pat. Nos. 5,120,420; 5,141,868; 5,437,999; 5,192,415; 5,264,103; and 5,575,895, the disclosures of which are hereby incorporated by reference.

We claim:

1. A test strip, having an indentation along an edge for tactile identification of a sample application port, said test strip comprising:
   a first insulating substrate having first and second surfaces, an indentation along an edge and a vent hole;
   at least two electrically conductive tracks affixed to the first surface of the first insulating substrate;
   a second insulating substrate having first and second surfaces, an indentation along an edge, and first and second openings, the second surface being affixed to the conductive tracks and the first surface of the first insulating substrate, the first opening exposing a portion of the conductive tracks for electrical connection to a meter capable of measuring an electrical property, the second opening being located along said edge and exposing a different portion of the conductive tracks and the vent hole;
   a test reagent overlaying at least a portion of the conductive tracks exposed by the second opening; and
   a roof having first and second surfaces and an indentation along an edge, the second surface of the roof being affixed to the first surface of the second insulating substrate and positioned so that the second surface of the roof and the surface of the first insulating substrate form opposing walls of a capillary fill chamber with a sample application port at said edge of the second insulating substrate, wherein the second opening in the second insulating substrate and the indentations in the first insulating substrate, the second insulating substrate, and the roof are aligned to thereby provide for tactile identification of the sample application port.

2. The test strip of claim 1, wherein the second surface of the roof includes a hydrophilic coating.

3. The test strip of claim 1, wherein the test reagent includes
   reaction components appropriate for performing a test and from about 1.75% by weight to about 17.5% by weight polyethylene oxide having a mean molecular weight from about 100 kilodaltons to about 900 kilodaltons,
   wherein the reagent will redissolve or resuspend upon addition of an aqueous test sample to the reagent.

4. The test strip of claim 1, wherein the test reagent includes reaction components appropriate for performing a test, and a dissolvable or suspendable film forming mixture including from about 0.2% by weight to about 2% by weight polyethylene oxide having a mean molecular weight from about 100 kilodaltons to about 900 kilodaltons,
   wherein the test reagent may be applied to the test strip in a wet form, may be subsequently dried, and then redissolved or resuspended upon addition of an aqueous test sample to the dried reagent.

5. The test strip of claim 4, wherein the second surface of the roof includes a hydrophilic coating.

6. The test strip of claim 1, wherein the roof has a solid transparent or translucent window, which is dimensioned and positioned so that the window overlays the entire width of the electrically conductive track that is closest to the indentation of the first insulating substrate and at least about ten percent of the width of the other electrically conductive track.

7. The test strip of claim 6, wherein the second surface of the roof includes a hydrophilic coating.

8. The test strip of claim 6, wherein the test reagent includes
   reaction components appropriate for performing a test and from about 1.75% by weight to about 17.5% by weight polyethylene oxide having a mean molecular weight from about 100 kilodaltons to about 900 kilodaltons,
   wherein the reagent will redissolve or resuspend upon addition of an aqueous test sample to the reagent.

9. The test strip of claim 6, wherein the test reagent includes reaction components appropriate for performing a test, and a dissolvable or suspendable film forming mixture including from about 0.2% by weight to about 2% by weight polyethylene oxide having a mean molecular weight from about 100 kilodaltons to about 900 kilodaltons,
   wherein the test reagent may be applied to the test strip in a wet form, may be subsequently dried, and then redissolved or resuspended upon addition of an aqueous test sample to the dried reagent.

10. The test strip of claim 9, wherein the second surface of the roof includes a hydrophilic coating.

11. The test strip of claim 1, further comprising:
    a first notch along the indentation in the first insulating substrate, and a notch along the indentation in the roof, both first and second notches being positioned so that they overlay one another.

12. The test strip of claim 11, wherein the second surface of the roof includes a hydrophilic coating.

13. The test strip of claim 11, wherein the test reagent includes
    reaction components appropriate for performing a test and from about 1.75% by weight to about 17.5% by weight polyethylene oxide having a mean molecular weight from about 100 kilodaltons to about 900 kilodaltons,
    wherein the reagent will redissolve or resuspend upon addition of an aqueous test sample to the reagent.

14. The test strip of claim 11, wherein the test reagent includes reaction components appropriate for performing a test, and a dissolvable or suspendable film forming mixture including from about 0.2% by weight to about 2% by weight polyethylene oxide having a mean molecular weight from about 100 kilodaltons to about 900 kilodaltons,
    wherein the test reagent may be applied to the test strip in a wet form, may be subsequently dried, and then redissolved or resuspended upon addition of an aqueous test sample to the dried reagent.

15. The test strip of claim 14, wherein the second surface of the roof includes a hydrophilic coating.

16. The test strip of claim 11 wherein the roof has a solid transparent or translucent window, which is dimensioned and positioned so that the window overlays the entire width of the electrically conductive track that is closest to the indentation of the first insulating substrate and at least about ten percent of the width of the other electrically conductive track.

17. The test strip of claim 16, wherein the second surface of the roof includes a hydrophilic coating.

18. The test strip of claim 16, wherein the test reagent includes reaction components appropriate for performing a test, and a dissolvable or suspendable film forming mixture including from about 0.2% by weight to about 2% by weight polyethylene oxide having a mean molecular weight from about 100 kilodaltons to about 900 kilodaltons, wherein the test reagent may be applied to the test strip in a wet form, may be subsequently dried, and then redissolved or resuspended upon addition of an aqueous test sample to the dried reagent.

19. The test strip of claim 18, wherein the second surface of the roof includes a hydrophilic coating.

20. The test strip of claim 16, wherein the test reagent includes reaction components appropriate for the test, and a dissolvable or suspendable film forming mixture including from about 0.2% weight to about 2% by weight polyethylene oxide having a mean molecular weight of 300 kilodaltons.

21. The test strip of claim 20, wherein the polyethylene oxide is about 0.71% by weight.

22. The test strip of claim 16, wherein the test reagent includes reaction components appropriate for performing a test and from about 1.75% by weight to about 17.5% by weight polyethylene oxide having a mean molecular weight from about 100 kilodaltons to about 900 kilodaltons, wherein the reagent will redissolve or resuspend upon addition of an aqueous test sample to the reagent.

23. The test strip of claim 22, wherein the mean molecular weight of the polyethylene oxide is 300 kilodaltons.

24. The test strip of claim 23, wherein the amount of polyethylene oxide, in the reagent is about 6.2% by weight.

25. A test strip comprising:

a first insulating substrate having first and second surfaces, a notch along an edge, and a vent hole;

at least two electrically conductive tracks affixed to the first surface of the first insulating substrate;

a second insulating substrate having first and second surfaces and first and second openings, the second surface being affixed to the conductive tracks and the first surface of the first insulating substrate, the first opening exposing a portion of the conductive tracks for electrical connection to a meter capable of measuring an electrical property, the second opening being located along an edge of the second insulating substrate and exposing a different portion of the conductive tracks, the notch in the first insulating substrate, and the vent hole;

a test reagent overlaying at least a portion of the conductive tracks exposed by the second opening; and a roof having first and second surfaces and a notch along an edge, the second surface of the roof being affixed to the first surface of the second insulating substrate and positioned so that 1) the second surface of the roof and the first surface of the first insulating substrate form opposing walls of a capillary fill chamber with a sample application port at said edge of the second insulating substrate, and 2) the notch in the roof overlays the notch in the first insulating substrate;

whereby the notch in the roof and the notch in the first insulating substrate will cause a liquid aqueous sample, when touched to the sample application port, to flow into the capillary chamber without significant hesitation.

26. A test strip, comprising:

a first insulating substrate having first and second surfaces and a vent hole;

at least two electrically conductive tracks affixed to the first surface of the first insulating substrate;

a second insulating substrate having first and second surfaces and first and second openings, the second surface being affixed to the conductive tracks and the first surface of the first insulating substrate, the first opening exposing a portion of the conductive tracks for electrical connection to a meter capable of measuring an electrical property, the second opening being located along an edge of the second insulating substrate and exposing a different portion of the conductive tracks and the vent hole;

a test reagent overlaying at least a portion of the conductive tracks exposed by the second opening; and a roof having first and second surfaces and a solid transparent or translucent window, the second surface of the roof being affixed to the first surface of the second insulating substrate and positioned so that it overlays the second opening of the second insulating substrate and so that the second surface of the roof and the first surface of the first insulating substrate form opposing walls of a capillary fill chamber with a sample application port at said edge of the second insulating substrate, and the transparent or translucent window being dimensioned and positioned so that the window extends from the sample application port, and overlays the entire width of one of the electrically conductive tracks and at least about ten percent of the width of the other electrically conductive track.

27. A test strip, having an indentation along an edge for tactile identification of a sample application port, said test strip comprising:

a first insulating substrate having first and second surfaces and an indentation along an edge;

at least two electrically conductive tracks affixed to the first surface of the first insulating substrate;

a second insulating substrate having first and second surfaces, an indentation along an edge and an opening, the second surface being affixed to the conductive tracks and the first surface of the first insulating substrate, the second insulating substrate configured to expose a portion of the conductive tracks for electrical connection to a meter capable of measuring an electrical property, the opening being located along said edge and exposing a different portion of the conductive tracks;

a test reagent overlaying at least a portion of the conductive tracks exposed by the opening;

a roof having first and second surfaces and an indentation along an edge, the second surface of the roof being affixed to the first surface of the second insulating substrate and positioned so as to overlay the opening and so that the second surface of the roof and the first surface of the first insulating substrate form opposing walls of a capillary fill chamber with a sample application port at said edge of the second insulating substrate; and a vent hole communicating with the capillary fill chamber;

wherein the opening in the second insulating substrate and the indentations in the first insulating substrate, the second insulating substrate, and the roof are aligned to thereby provide for tactile identification of the sample application port.

28. The test strip of claim 27, wherein the roof has a solid transparent or translucent window, which is dimensioned and positioned so that the window overlays the entire width of the electrically conductive track that is closest to the indentation of the first insulating substrate and at least about ten percent of the width of the other electrically conductive track.

29. The test strip of claim 27 further comprising a first notch along the indentation of the first insulating substrate, and a notch along the indentation in the roof, both first and second notches being positioned so that they overlay one another.

30. The test strip of claim 29 wherein the roof has a solid transparent or translucent window, which is dimensioned and positioned so that the window overlays the entire width of the electrically conductive track that is closest to the indentation of the first insulating substrate and at least about ten percent of the width of the other electrically conductive track.

31. A test strip comprising:
   a first insulating substrate having first and second surfaces and a notch along an edge;
   at least two electrically conductive tracks affixed to the first surface of the first insulating substrate;
   a second insulating substrate having first and second surfaces and an opening, the second surface being affixed to the conductive tracks and the first surface of the first insulating substrate, the second insulating substrate configured to expose a portion of the conductive tracks for electrical connection to a meter capable of measuring an electrical property, the opening being located along an edge of the second insulating substrate and exposing a different portion of the conductive tracks, aid overlaying the notch in the first insulating substrate;
   a test reagent overlaying at least a portion of the conductive tracks exposed by the opening;
   a roof having first and second surfaces and a notch along an edge, the second surface of the roof being affixed to the first surface of the second insulating substrate and positioned so that 1) the second surface of the roof and the first surface of the first insulating substrate form opposing walls of a capillary fill chamber with a sample application port at said edge of the second insulating substrate, and 2) the notch in the roof overlays the notch in the first insulating substrate; and
   a vent hole communicating with the capillary fill chamber;
   whereby the notch in the roof and the notch in the first insulating substrate will cause a liquid aqueous sample, when touched to the sample application port, to flow into the capillary chamber without significant hesitation.

32. A test strip comprising:
   a first insulating substrate having first and second surfaces;
   at least two electrically conductive tracks affixed to the first surface of the first insulating substrate;
   a second insulating substrate having first and second surfaces and an opening, the second surface being affixed to the conductive tracks and the first surface of the first insulating substrate, the second insulating substrate configured to expose a portion of the conductive tracks for electrical connection to a meter capable of measuring an electrical property, the opening being located along an edge of the second insulating substrate and exposing a different portion of the conductive tracks;
   a test reagent overlaying at least a portion of the conductive tracks exposed by the opening;
   a roof having first and second surfaces and a solid transparent or translucent window, the second surface of the roof being affixed to the first surface of the second insulating substrate and positioned so that it overlays the opening of the second insulating substrate and so that the second surface of the roof and the first surface of the first insulating substrate form opposing walls of a capillary fill chamber with a sample application port at said edge of the second insulating substrate, and the transparent or translucent window being dimensioned and positioned so that the window extends from the sample application port, and overlays the entire width of one of the electrically conductive tracks and at least about ten percent of the width of the other electrically conductive track; and
   a vent hole communicating with the capillary fill chamber.

* * * * *